US009439439B2

(12) United States Patent
Borrelli et al.

(10) Patent No.: US 9,439,439 B2
(45) Date of Patent: *Sep. 13, 2016

(54) ANTIMICROBIAL ACTION OF CU, CUO AND CU$_2$O NANOPARTICLES ON GLASS SURFACES AND DURABLE COATINGS

(71) Applicant: CORNING INCORPORATED, Corning, NY (US)

(72) Inventors: Nicholas Francis Borrelli, Elmira, NY (US); Odessa Natalie Petzold, Elmira, NY (US); Joseph Francis Schroeder, III, Corning, NY (US); Wageesha Senaratne, Horseheads, NY (US); Florence Christine Monique Verrier, Corning, NY (US); Ying Wei, Painted Post, NY (US)

(73) Assignee: Corning Incorporated, Corning, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/682,452

(22) Filed: Apr. 9, 2015

(65) Prior Publication Data

US 2015/0208664 A1 Jul. 30, 2015

Related U.S. Application Data

(63) Continuation of application No. 14/007,781, filed as application No. PCT/US2012/030863 on Mar. 28, 2012, now Pat. No. 9,028,962.

(60) Provisional application No. 61/468,173, filed on Mar. 28, 2011, provisional application No. 61/532,346, filed on Sep. 8, 2011.

(51) Int. Cl.
*B32B 3/00* (2006.01)
*A01N 59/20* (2006.01)
(Continued)

(52) U.S. Cl.
CPC .............. *A01N 59/20* (2013.01); *A01N 25/08* (2013.01); *C03C 17/006* (2013.01);
(Continued)

(58) Field of Classification Search
CPC .... A01N 59/16; A01N 59/20; C03C 21/002; C03C 2217/42; C03C 2217/007; C03C 2217/475; C03C 17/005; C03C 17/06; Y10T 428/31; Y10T 428/315; Y10T 428/2927; Y10T 428/24926; Y10T 428/24909
See application file for complete search history.

(56) References Cited

U.S. PATENT DOCUMENTS
4,018,612 A 4/1977 Chyung
5,665,134 A 9/1997 Kirby et al.
(Continued)

FOREIGN PATENT DOCUMENTS
DE 202005006784 10/2005
EP 1270527 7/2001
(Continued)

OTHER PUBLICATIONS
Application No. 201280015236.1, Chinese Search Report, Jun. 15, 2015.
(Continued)

*Primary Examiner* — Elizabeth Mulvaney
(74) *Attorney, Agent, or Firm* — Payal A. Patel (57) ABSTRACT

A transparent cover glass for applications such as, but not limited to, touch screen devices that embody antimicrobial properties that include s being antibacterial, antifungal, and antiviral. The antimicrobial glasses contain nanoparticles of Cu or Cu$_2$O on the surface of the glass. The antimicrobial glasses can further have a fluorosilane coating or other coating on the surface to make the glasses easy-to-clean. Also, glass surfaces having an antibacterial or antimicrobial surfaces and a protective coating on the surface that do not inhibit the antibacterial or antimicrobial properties of the glass are described. The disclosure is further directed to methods of making such articles.

12 Claims, 6 Drawing Sheets

(51) Int. Cl.
| | |
|---|---|
| *C03C 17/00* | (2006.01) |
| *C03C 17/42* | (2006.01) |
| *C03C 21/00* | (2006.01) |
| *C03C 17/36* | (2006.01) |
| *A01N 25/08* | (2006.01) |

(52) U.S. Cl.
CPC ........ *C03C 17/007* (2013.01); *C03C 17/3692* (2013.01); *C03C 17/42* (2013.01); *C03C 21/002* (2013.01); *C03C 2217/228* (2013.01); *C03C 2217/253* (2013.01); *C03C 2217/42* (2013.01); *C03C 2217/475* (2013.01); *C03C 2217/48* (2013.01); *C03C 2218/322* (2013.01); *C03C 2218/324* (2013.01); *Y10T 428/24909* (2015.01); *Y10T 428/24926* (2015.01); *Y10T 428/259* (2015.01); *Y10T 428/265* (2015.01); *Y10T 428/31544* (2015.04)

(56) References Cited

U.S. PATENT DOCUMENTS

| | | | |
|---|---|---|---|
| 7,192,602 | B2 | 3/2007 | Fechner et al. |
| 7,763,362 | B2 | 7/2010 | Jablonski et al. |
| 8,973,401 | B2 | 3/2015 | Borrelli et al. |
| 2004/0253321 | A1 | 12/2004 | Fechner et al. |
| 2006/0142413 | A1 | 6/2006 | Zimmer et al. |
| 2006/0172877 | A1 | 8/2006 | Fechner et al. |
| 2007/0026089 | A1 | 2/2007 | Hu |
| 2007/0172661 | A1* | 7/2007 | Fechner ................ A01N 59/16 428/409 |
| 2007/0254163 | A1 | 11/2007 | Veerasamy et al. |
| 2010/0015193 | A1 | 1/2010 | Inaoka et al. |
| 2010/0221307 | A1 | 9/2010 | Matsushita et al. |
| 2011/0062849 | A1 | 3/2011 | Carlson et al. |
| 2012/0107558 | A1 | 5/2012 | Koval et al. |
| 2014/0079807 | A1 | 3/2014 | Borrelli et al. |

FOREIGN PATENT DOCUMENTS

| | | |
|---|---|---|
| EP | 1748353 | 7/2005 |
| EP | 2088131 A | 8/2009 |
| JP | 2005119026 | 5/2005 |
| JP | 2005119026 | 12/2005 |
| JP | 2009173641 | 8/2009 |
| WO | 0151426 | 7/2001 |
| WO | 2015/115151 | 12/2005 |
| WO | 2005115151 A | 12/2005 |
| WO | 2006099906 | 9/2006 |
| WO | 2007095058 | 8/2007 |
| WO | 2008047810 | 4/2008 |
| WO | 2009070237 | 6/2009 |
| WO | 2010073738 | 7/2010 |
| WO | 2012061240 | 5/2012 |

OTHER PUBLICATIONS

Zhang, et al., Antibacterial Properties of AISI 420 Stainless Steel Implanted by Ag/Cu ions, IEEE vol. 4244-3544-9, (2010). pp. 978-1, 978-2.
M. Dubiel, et al., Ag/Na ion exchange in soda-lime glasses and the formation of small Ag nanoparticles, Materials Science and Engineering B 149 (2008) pp. 146-151.
D. Ritchie, Copper-containing Fungicides/bactericides and their use in Management of Bacterial Spot on Peaches, Southeast Region Newsletter, vol. 4., No. 1 (Mar. 2004).
L. Esteban-Tejeda, Antibacterial and antifungal activity of a soda-lime glass containing copper nanoparticles, Nanatechnology 20 (2009) 505701 (6pp).
J.O. Noyce et al, "Inactivation of influenza A virus on copper versus stainless steel surfaces". Appl. Environ. Microbiol. vol. 73 (2007) pp. 2748-2750.
Patent Cooperation Treaty International Notification of Transmittal of the International Search Report and the Written Opinion of the International Searching Authority, international application No. PCT/US2012/030863: mailing date Sep. 28, 2012, 13 pages.
J.L. Sagripanti, "Mechanism of copper-mediated inactivation of herpes simplex virus," Antimicrob. Agents Chemother.., vol. 41 (1997), pp. 12-817.
Horie, et al., Inactivation and morphological changes of avian influenza virus by cooper ions, Arch Virol 153:1467-1472.
Haldar, et al. Preparation, application and testing of permanent antibacterial and antiviral coatings, Dept. of Chemistry and Department of Bioengineering, (Sep. 2007).
Borkow et al; "Copper, an Ancient Remedy Returning to Fight Microbial, Fungal and Viral Infections"; Current Chemical Biology, 2009, 3, 272-278.
Borkow et al, "Copper as a Biocidal Tool," Current Med. Chem. Vol. 12 (2005), pp. 2163-2175.
Borkow et al; "A Novel Anti-Influenza Copper Oxide Containing Respiratory Face Mask"; PLOS ONE, June 2010, vol. 5, Issue 6.
Jordan et al, "The Influence of Copper on the Survival of Infectious Bronchitis Vaccine Virus in Water"; Vet. Rec. 1971, 89:23, 609-610 n.
JP2014502735 Office Action Dated February 23, 2016.
Totsuka et al; "The Effects of Amino Acids and Metals on the Infectivity of Poliovirus Ribonucleic Acid"; Japan J. Microbiol. 1974, 18 (2), 107-112.
TW101110865 Search Report Dated Oct. 26, 2015.
Yamamoto et al; "Mechanism of Inactivation of Bacteriophages by Metals"; Biochem. Biophys. ACTA. 2001, 91, 257.

* cited by examiner

ANTIMICROBIAL ACTION OF CU, CUO AND CU₂O NANOPARTICLES ON GLASS SURFACES AND DURABLE COATINGS

CROSS-REFERENCE TO RELATED APPLICATIONS

This application is a continuation of U.S. patent application Ser. No. 14/007,781 filed on Sep. 26, 2013, which claims the benefit of priority under 35 U.S.C. §371 of International Application Serial No. PCT/US12/30863, filed on Mar. 28, 2012, which, in turn, claims the benefit of priority of U.S. Provisional Patent Application Ser. No. 61/468,173, filed on Mar. 28, 2011 and to U.S. Provisional Patent Application Ser. No. 61/532,346, filed on Sep. 8, 2011, the contents of which are relied upon and incorporated herein by reference in their entireties as if fully set forth below.

FIELD

Embodiments are directed to the production of glass whose surfaces have antimicrobial activity, and in particular to glass surfaces containing copper and/or copper oxides. Embodiments are further directed to the making of such copper-containing glass. Other embodiments are directed to a protective coating on the surface that does not inhibit the antimicrobial properties of the glass.

BACKGROUND

The biological activity of copper is to a large part due to its ability to exist in what is termed the "free" state as metallic copper or "ionic" state as a copper salt or oxide. While copper is almost always combined with other elements or minerals, under certain conditions copper can exist in the ionic or free copper state, both of which are biologically active and thus gives copper the ability to kill bacteria, viruses and fungi.

Copper and its salts and oxides, have been used since antiquity to treat a wide variety of ailments and injuries. The earliest recorded medical use of copper is found in an Egyptian medical text known as the Smith Papyrus, written between 2600 and 2200 B.C., which describes using copper to sterilize chest wounds and drinking water. Other early texts such as the Ebers Papyrus (written around 1500 B.C.), De Materia Medica by Dioscrides, De Medicina by Aulus Cornelius Celsus at the time of the first Roman emperors, and works Pliny and Hippocrates also describe the medicinal use of copper, in metallic form or as a salt or oxide. The materials mentioned in the early texts include copper carbonate (probably as the mineral malachite), copper chloride that was formed by the action of salt water on metallic copper, verdigris that is formed by the action of hot vinegar (acetic acid) vapors on metallic copper, and blue vitrol which is copper sulfate. Copper, in metallic form or as a salt or oxide, was used to treat burn wounds, itching headaches, trembling limbs, boils and other maladies as bloodshot eyes, inflamed or bloodshot eyes, cataracts, "fat in the eyes" (possibly trachoma), and cataracts. The Greeks treated wounds with a dry powdered mixture of copper oxide and copper sulfate and also a boiled mixture of red copper oxide (cuprous oxide, $Cu_2O$) and honey. Black copper oxide mixed with honey was used to remove intestinal worms and, in diluted form, was also used to clear the head by administrations as nose drops, as a stomach purge when drunk as a honey and water mixture, used as eye drops to remove pain, and as a rinse for canker sores. In the Americas the Aztecs treated sore throat by gargling with a mixture copper and other ingredients. In India copper was used to treat lung diseases and in ancient Persia powdered copper carbonate was sprinkled on boils, and copper acetate and copper oxide were used for diseases of the eye. In addition, for many centuries it was known that water could be transported in copper containers with little or no slime formation. When wooden or clay water vessels were used as a water carrier a copper coin or bar was placed in the vessel for the same purpose, this particular practice being widely used by those traveling across the American West in the 1800s.

With the discovery of the existence of microbes in the 1800s, the antimicrobial properties of copper and its compounds became more widely investigated, and these investigations continue to the present day. A few examples of the literature are articles by J.O Noyce et al, "Inactivation of influenza A virus on copper versus stainless steel surfaces," Applied Environmental Microbiology, Vol. 73 (2007), pages 2748-2750; J.L. Sagripanti et al. Mechanism of copper-mediated inactivation of herpes virus," Antimicrob Agents Chemotherapy Vol. 41 (1997), pages 8122-817; G. Borkow et al, "Copper as a biocidal tool," Current Med. Chem. Vol. 12 (2005), pages 2163-2175; U.S. Patent Application Publication No. 2001-0221307 (antiviral agents, antiviral fibers and antiviral fiber structures; U.S. Pat. No. 7,192,602 for Walter-insoluble, antimicrobial silicate glass and use thereof; and L. Esteban-Tejeda et al, "Antibacterial and antifungal activity of a soda-lime glass containing copper nanoparticles," Nanotechnology, Vol. 20 (2009) 505701 (6 pages).

Although there is mention of copper, $Cu^0$, and cupric ions, $Cu^{+2}$, as an antimicrobial agents in various forms and applications, for the most part it consists of generalized comments without a real description of the specific nature of how the copper species was employed (see references below); for example, as a film, solution, particle etc. See G. Borkow et al, Copper as a biocidal tool," Current Med. Chem. Vol. 12 (2005); pages 2163-2175; N. Yamamoto et al, *Biochem. Biophys. Acta.* 2001, 91, 257; F.T. Jordan et al, *Vet. Rec.* 1971, 89, 609; and A Totsuka, et al, *Jpn. J. Microbiol.* 1974, 18, 107. In addition, there are only a few references that mention that the effect of the oxidation of $Cu^0$ to CuO is a lessening the antimicrobial action of the substrate. The oxidation of $Cu^0$ to CuO is well known and is typically prevented by use of a protective film coating that is placed on top of a $Cu^0$ layer. However, in addition to protecting the $Cu^0$ surface from oxidation, for antibacterial or antimicrobial uses, the coating must be one that will not inhibit the antimicrobial or antimicrobial activity of the article. Stated another way, the protective film has to be effective is protecting the surface from oxidation while maintaining antibacterial or antimicrobial action. No mention has been made of the use of cuprous oxide, $Cu_2O$, particularly $Cu_2O$ nanoparticles, as an antimicrobial agent in or on glass. Further, no mention was made in the articles of having a protective coating over the copper nanoparticles that would serve to diminish or slow down the degradation of the nanoparticles' antibacterial or antimicrobial activity.

In the last twenty to thirty years touch screen devices have become prevalent in society, first appearing on automatic teller machines and later on vending machines, cell phone, computers, personal electronic devices, and more. With the higher concentrations of people in cities, along with the high mobility throughout the world, there has been rising concern about the transmittal of microbes. While microbes can be removed or killed by the proper cleaning of surfaces using an appropriate biocide, this is often not truly practical solution because many persons can use a given device in a short time period and device cannot be continually cleaned. Consequently, it is highly desirable to have surfaces that are durable and also possess antimicrobial properties that last over a period of time before they are cleaned so that different persons using a device are equally protected. Embodiments are directed to this end.

SUMMARY

Embodiments are directed to providing the antimicrobial property of Cu to a glass through the deposition of Cu-containing nanoparticles to the surface of glass. The processes by which this can be accomplished are dip-coating, spin coating, slot coating, curtain coating or spray coating onto the surface of the glass from a suspension of Cu, $Cu_2O$ or CuO nanoparticles in water or solvent. The glass is then heated in an air or an inert atmosphere (for example, nitrogen or helium) to a temperature sufficient to seal the particles to the glass. In an embodiment of a process using CuO as the initial nanoparticles, the process includes a subsequent step to reduce the CuO to Cu nanoparticles. The nanoparticle composition and concentration of nanoparticles on the surface of a transparent substrate such as glass determine the ultimate optical transmission. Consequently it is possible to provide antimicrobial action to an otherwise transparent glass, including a glass that has been thermally or chemically strengthened glass, for example, chemically strengthened by ion-exchanges of larger cations from an ion-exchange bath for smaller cations present in the glass. In addition, a coating of a material that facilitates the easy cleaning of the surface of the glass, for example a fluorosilane compound, or other coating that resists or minimizes the effects of fingerprint transfer or smudging, can be applied to the nanoparticle containing glass surface without affecting the antimicrobial function.

With regard to Cu, CuO, and $Cu_2O$, all have shown antibacterial behavior at different surface concentrations, but only Cu have shown antiviral behavior. CuO is not an antiviral material, therefore, in order to have an antimicrobial effect, in the case of using CuO as the initial nanoparticle, it is necessary to have a reduction step, after sintering and/or ion-exchange, the Cu-containing nanoparticles particles on the glass or other substrate are reduced to Cu or $Cu_2O$ nanoparticles. In one embodiment the nanoparticles are reduced to Cu nanoparticles. The Cu nanoparticle composition and concentration placed on the glass or other substrate can be tuned to an optimized optical transmission so it is possible to provide antimicrobial action to an otherwise transparent glass and chemically strengthened glass or other substrate.

In a further embodiment, in the methods a final coating of an easy-to-clean material, for example a fluorosilane material, can be applied to the glass article after ion-exchange without affecting the antimicrobial function of the article.

One embodiment is directed to antimicrobial glass articles having selected metal nanoparticles deposited on the surface of the glass with a selected protective layer deposited on top, wherein the protective layer that diminishes or slows down the degradation of the nanoparticles' antimicrobial activity. Oxidation of the nanoparticles is the primary cause of the diminishing or slowing down of the nanoparticles' antimicrobial activity. In one embodiment, the metal nanoparticles are selected from the group consisting of copper(0), silver (0), nickel(0), platinum(0), palladium (0), gold(0) and zinc (0) particles. The selected protective coating is selected from the group consisting of sodium silicates (NaSil) and poly siloxanes/silsesquioxanes. In one embodiment, the glass articles having the nanoparticles and protective coating therein further have an easy-to-clean layer on top of the protective coating layer to facilitate the removal of oils, for example, fingerprint oils.

As described above, some embodiments are directed to methods for making glass articles having the antimicrobial metal nanoparticle surface with a protective coating over the metal nanoparticle surface/coating. In one embodiment, the method comprises the deposition of the metal oxide nanoparticle coating accomplished by dip-coating, spin coating, spraying or other coating method(s) that are capable of depositing a suspension of CuO or $Cu_2O$ nanoparticles in water, or other suitable fluid, onto a surface of the glass and drying the suspension on the surface. Drying is carried out at a temperature in the range of 100° C. to 150° C., preferably at a temperature in the range of 110° c. to 130° C. The drying time is in the range of 1 hour to 4 hours. Then the protective coating is deposited on the surface of the oxide nanoparticle containing article, followed by a second drying step at a temperature in the range of 120° c. to 300° C. The drying time is in the range of 1 hour to 4 hours. In subsequent steps the glass article having both the nanoparticles and protective coating thereon are sintered in air or an inert atmosphere such as a nitrogen atmosphere, subjected to an ion-exchange process, if the glass contain exchangeable ions, to impart a compressive stress in the glass from the surface to a selected depth, and finally subject to a reductions step, using hydrogen or other reducing gas or gas mixture, to reduce the oxide nanoparticles to copper.

In another embodiment, the method comprises providing a mixture of copper oxide-containing nanoparticles and the protective material suspended in an appropriate fluid, for example without limitation, water, and with or without a surfactant and/or a polymer carrier material in the fluid/nanoparticle suspension, is deposited on a surface of a glass article and dried. Drying is carried out at a temperature in the range of 100° C. to 150° C., preferably at a temperature in the range of 110° C. to 130° C. The drying time is in the range of 1 hour to 4 hours. The nanoparticle/protective coating, with or without the surfactant and/or polymer carrier material can be applied by spraying, spin-coating or dip-coating. In subsequent steps the glass article having both the nanoparticles and protective coating thereon are sintered in air or an inert atmosphere such as a nitrogen atmosphere, subjected to an ion-exchange process, if the glass contains exchangeable ions, to impart a compressive stress in the glass from the surface to a selected depth, and finally subject to a reductions step, using hydrogen or other reducing gas or gas mixture, to reduce the nanoparticles to copper.

The protective coating in the above product and methods of preparing the products also acts to adhere the nanoparticles to the substrates.

Embodiments may provide a number of advantages to glasses that are used in any "touch" application; for example without limitation, as a touch screen in cell phones, computers and automatic teller machines. The glasses in such application can be an ion-exchanged glass or a glass that is not ion exchanged. Thus, using the teachings provided herein, it is possible to: provide antimicrobial activity to a transparent glass for application where it is necessary to see through the glass; provide antimicrobial activity to a chemically strengthened glass; and provide antimicrobial activity when additional functional coating(s) have been applied to the glass, for example, fluorosilanes or other coating to enhance the cleanability of the glass, resist or minimize fingerprint transfer or smudging, or impart hydrophobicity, or oleophobicity, or both.

Ideally, all three properties will be manifested resulting in an article or an article having a surface that exhibits antimicrobial behavior in a strengthened glass whose touch surfaces have easy-to-clean properties, and/or anti-smudge/anti-fingerprint properties and the glass remains transparent.

DETAILED DESCRIPTION

Herein all percentages are in weight percent, wt %, unless specified otherwise.

As used herein the term "antimicrobial," means an agent or material, or a surface containing the agent or material that will kill or inhibit the growth of microbes from at least two of families consisting of bacteria, viruses and fungi. The term as used herein does not mean it will kill or inhibit the growth of all species microbes within such families, but that it will kill or inhibit the growth or one or more species of microbes from such families. When an agent is described as being "antibacterial, or "antiviral" or "antifungal," it means that the agent will kill or inhibit the growth of only bacteria, viruses or fungi, respectively. All the samples identified in this disclosure were prepared using commercially available Corning 2318 aluminosilicate glass (Corning Incorporated).

Also herein we use the tem "NaSil" as a generic designation for sodium silicates and the term "MS" as a generic designation for poly siloxanes/silsesquioxanes.

As used herein the term "Log "Reduction" or "LR" means $-Log (C_a/C_0)$, where $C_a$=the colony form unit (CFU) number of the antimicrobial surface containing Cu nanoparticles and $C_0$=the colony form unit (CFU) of the control glass surface that does not contain Cu nanoparticles. That is:

$$LR=-Log(C_a/C_0),$$

As an example, a Log Reduction of 3=99.9% of the bacteria or virus killed and a Log Reduction of 5=99.999% of bacteria or virus killed.

Utilizing the present disclosure it is possible to make a transparent cover glass for applications such as, but not limited to, touch screen devices that embodies antimicrobial properties (antimicrobial is the term used to include all of the following: antibacterial, antifungal, and antiviral). Moreover, for such antimicrobial applications additional requirements are necessary, among which are a way to keep the surface clean (handling can seriously limit the antimicrobial activity) and mechanical strength as afforded by chemical means such as ion-exchange ("IX"), the durability of any coating placed on the antimicrobial glass, and the non-interference or minimal interference of any coating with the antimicrobial activity. Although it is well known that Ag and Cu can provide antimicrobial behavior to some extent, it is not at all obvious how to incorporate this antimicrobial behavior in combination with the other two above mentioned properties; and particularly to accomplish this so as to have the antimicrobial activity at a log reduction level of >3 (99.9%). It is here pointed out that although the reports of the antimicrobial activity of Ag and Cu is extensive, the particular way it is described varies widely, from ionic solution to doped glasses coated with particles. For the application intended here we are speaking of a smooth transparent glass surface that is capable of being made strong and cleanable in a format that will yield significant antimicrobial behavior. Moreover, little if any of the reported literature defines the level of activity in a rigorous way, let alone in terms of, for example, the concentration, particle size, etc. of the antimicrobial material.

In this disclosure we describe methods by which nanoparticles of CuO can be deposited onto a glass that can be IX strengthened, and additionally coated with a fluorosilane layer to keep clean while maintaining the high level of antimicrobial behavior. Direct deposition of $Cu_2O$ or Cu-nanoparticles, however accomplished, although producing the desired antimicrobial behavior will not suffice since the subsequent IX treatment is highly oxidizing and will oxidize the $Cu_2O$ or Cu-nanoparticle back to CuO. CuO nanoparticles can be shown to be antibacterial, but they are only weakly antiviral. To be described as antiviral the material must display this activity over a range of at least three viruses. In this disclosure we report on the antiviral activity of the antimicrobial glass described herein with respect to the following, Adenovirus, HSV (Herpes), and WSN (influenza A). Also in this disclosure we report the antibacterial activity of the antimicrobial glass described herein with respect to E. coli.

The present disclosure in one embodiment is directed to the antimicrobial property of Cu present on a glass surface through the deposition of CuO-containing nanoparticles to the surface of glass and their reduction to Cu nanoparticles. In another embodiment it is directed to the antimicrobial properties of $Cu_2O$ nanoparticles present on the glass surface which can be accomplished by the controlled oxidation of Cu nanoparticles on the glass surface. The depositing $Cu_2O$ or CuO nanoparticles processes can be accomplished are dip-coating, spin-coating or spray coating onto the surface of the glass from a suspension of $Cu_2O$ or CuO nanoparticles in water. In one embodiment, after deposition of the $Cu_2O$ or CuO nanoparticles the glass is then heated (an air or $N_2$) to a temperature sufficient to seal or bond the nanoparticles to the glass. When CuO is used as the initial nanoparticles deposited on the glass and bonded to it, there is a subsequent reduction step to reduce the CuO nanoparticles to Cu nanoparticles. In the examples herein the reduction is carried out in a hydrogen atmosphere. In another embodiment, after the reduction step the Cu-nanoparticles are autoclaved to form a mixture of Cu and $Cu_2O$ nanoparticles on the glass surface. The nanoparticle composition and concentration determines the ultimate optical transmission.

As a result, using the teachings presented herein. It is possible to provide antimicrobial action to an otherwise transparent glass and chemically strengthened glass. In one embodiment the glass compositions are selected from the group consisting of soda lime glass, alkali alumino silicate glasses and alkali aluminoborosilicate glasses. In a further embodiment, after the nanoparticles are in the form of Cu nanoparticles are present on the glass surface, the glass can be treated with a fluorosilane material to give it an easy-to-clean surface enabling the removal of an smudges or other matter from the surface of the glass without detriment to the antimicrobial properties of the glass surface. It should be made clear that the antimicrobial properties described herein can imparted to alkali aluminosilicate, alkali aluminoborosilicate and soda lime glasses whether they are chemically strengthened or non-chemically strengthened. Further, by using the methods described herein it is possible to either (1) start with a chemically strengthened glass and impart the antimicrobial properties to the glass or (2) to start with a non-chemically strengthened glass, impart the antimicrobial properties to the glass and then chemically strengthen the glass by ion-exchange.

Chemically strengthening a glass containing Cu nanoparticles as the antimicrobial agent is not a straightforward process. When the reduced Cu-nanoparticle sample is placed in a $KNO_3$ bath for chemical strengthening by ion-exchange, the result is that the Cu nanoparticles, while in the bath, are reoxidized to the CuO state. It is possible to restore the reoxidized CuO nanoparticles to the Cu state by repeating the $H_2$ reduction step, but this is not a satisfactory solution since the 450° C. reduction temperature reduces the strength of the ion-exchanges glass by relaxing the compression present in the glass. However, if ion-exchange must be carried out on a glass containing reoxidized Cu-nanoparticles, it is possible to minimize the effect of the hydrogen reduction on the chemical strengthening by carrying out the $H_2$ reduction at lower temperatures. For example, the reduction can be carried out at a temperature in the range of 250° C. to 350° C. For example, in one experiment the reduction of the reoxidized particles was carried out in hydrogen at 300° C. for a time in the range of 5 minutes to 2 hours.

In the examples given herein a colloidal copper (II) oxide dispersion (NanoArc® copper oxide, average primary particle size powder of 23-37 nm, 97.5%, Alfa Aesar, John Mathey Company) and the material was dispersed in deionized (DI) water to produce 0.5, 1, 2.5 and 5 wt % colloidal suspensions where the agglomerates have a size in the range of 100-200 nm. The colloidal suspensions were then sonicated, which aids in breaking up agglomerates, and then dip-coated onto an alkali aluminosilicate glass samples using the varying concentrations using withdrawal speeds from the dip-coating suspensions of 10, 25, 50 and 100 mm/min. The processing of the coated glass further breaks up agglomerates so the glass is substantially coated with nanoparticles. In dip-coating, contrary to intuition, the coating thickness generally increases with faster withdrawal speeds. The suspensions can also be made using tergitol as a surfactant and coated according to the methods described above.

After the samples were dip-coated they were dried at ambient temperature in for example, a laboratory fume hood to facilitate the passage or air over the samples. Alternative methods of drying are possible for example without limitation, drying in an oven having a flow of air therethrough at a temperature in the range of 30° C. and 120° C. After drying, the CuO nanoparticles were placed into an oven in a nitrogen atmosphere and sintered onto at a temperature in the range of 600-650° C. for a time in the range of 30 min-4 hours. In one embodiment the sintering was carried out at a temperature of approximately 625° C., for a time in the range of 1-2 hours. After the sintering selected samples were reduced in a hydrogen ($H_2$) atmosphere at temperature in the range of 300-450° C. for a time in the range of 0.5 to 8 hours. Hydrogen reduction can be carried out using mixtures of $H_2$ and an inert gas, for example, nitrogen or helium, or a commercially available forming gas can also be used. The reductions can also be carried out at $H_2$ pressures in the range of 1-5 atmospheres, preferable in the range of 1-3 atmospheres. In one embodiment, where ion exchange was not required, the reduction was carried out under $H_2$ at a temperature of approximately 450° C. for a time in the range of 1-5 hours. At this point the glass has Cu nanoparticles on the surface and will exhibit antimicrobial activity.

In one embodiment, the glass article has a transparency of 70% or above, for example, 80% or above, for example, 70% or above.

EXAMPLES

Specific Methods Used to Prepare an Antimicrobial Glass

Method 1 a) Spin-coat, spray coat or dip-coat CuO nanoparticles onto a glass that is ion-exchanged or can be ion-exchanged for example, Corning glass codes 2318, 3318, 0210 which are commercially available. b) Heat CuO-nanoparticle coated glass in $N_2$ at ambient pressure (1 atmosphere) at 625-650° C. for a time of 0.5-1 hours to sinter (attached or bond) the particles to the surface. (The temperature of the sintering is dependent on the glass composition). c) Chemically strengthen the sintered glass in an appropriate ion-exchange bath. d) Reduce the CuO nanoparticles to Cu-nanoparticles in $H_2$ at ambient pressure (1 atmosphere $H_2$) at low temperature, for example, at a temperature of 300° C. for a time in the range of 5 minutes to 2 hours. e) Apply a fluorosilane coating to yield an ion-exchanged glass having the reduced Cu-nanoparticles thereon.

Figure 1:
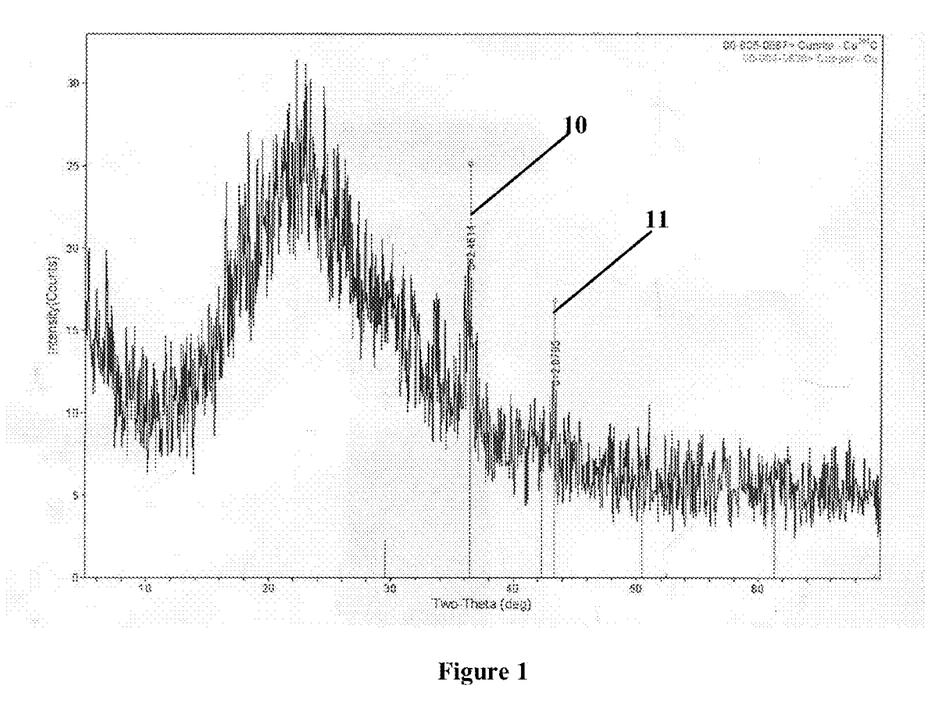
FIG. 1 is an x-ray diffraction pattern of a glass prepared according to Method 2 according to some embodiments.

Method 2 a) Spin-coat, spray coat or dip-coat CuO nanoparticles onto a potentially ion-exchanged glass, for example, Corning glass codes 2318, 3318, 0210) as in Method 1. b) Heat CuO-nanoparticle coated glass in $N_2$ at ambient pressure (1 atmosphere) to sinter (attached or bond) the particles to the surface, the temperature dependent on the glass as in Method 1. c) Reduce to Cu-nanoparticles in $H_2$ (300° C.). d) Strengthen the glass of c) by ion-exchange. e) Autoclave to yield an ion-exchanged glass having Cu and $Cu_2O$ nanoparticles thereon. FIG. 1 is an x-ray diffraction pattern of a glass prepared according to Method 2 with the Cu nanoparticle peak 11 and $Cu_2O$-nanoparticle peak 10 indicated.

Method 3 a) Spin-coat, spray coat or dip-coat CuO nanoparticles onto a potentially ion-exchanged glass, for example, Corning glass codes 2318, 3318, 0210 as in Method 1.) b) Heat in air or nitrogen to attach particles to surface and react with glass (>600° C.). c) Reduce to Cu-nanoparticles in $H_2$ (450° C.). d) Apply fluorosilane coating.

Figure 2A:
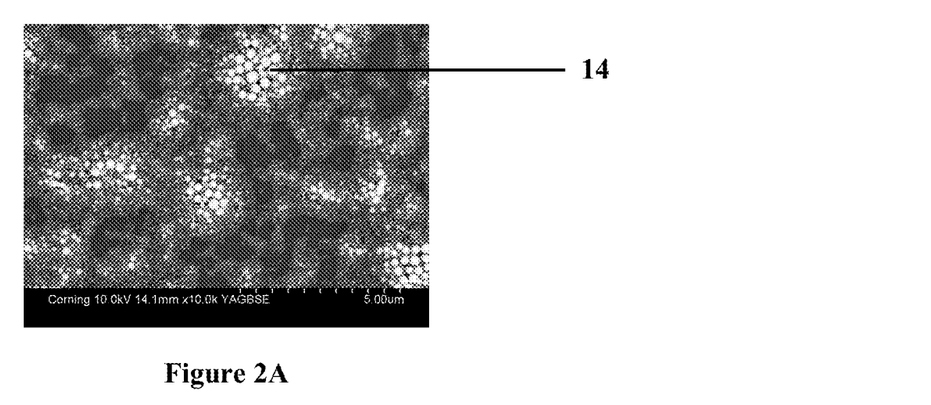
FIGS. 2A, 2B, and 2C are SEM microphotographs of glass surfaces made according to some embodiments.
Figure 2B:
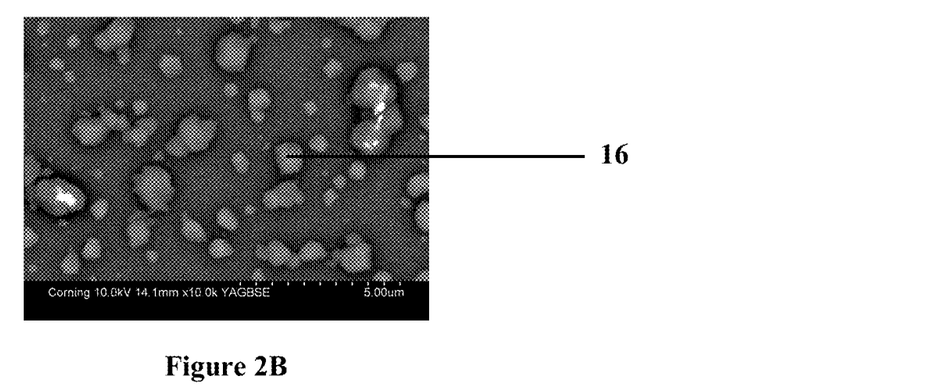
Figure 2C:
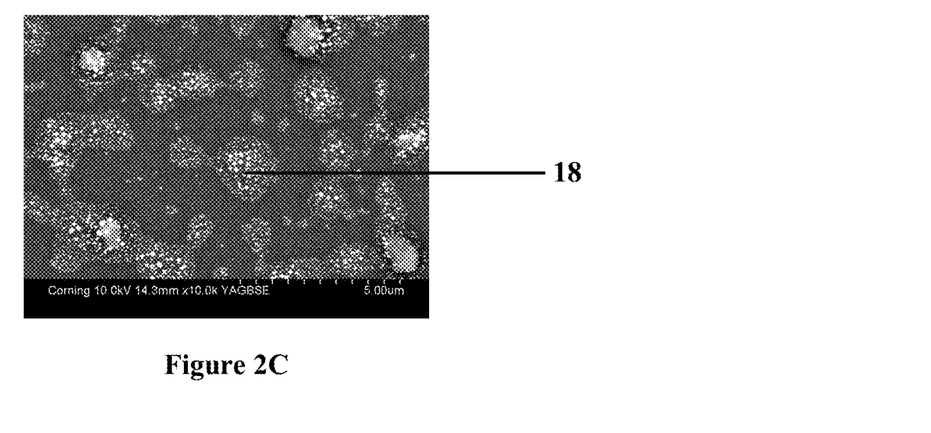

FIGS. 3A, 3B, and 3C are SEM microphotographs of glass surfaces after each stage listed above, according to some embodiments. In FIG. 2A, 14 represents the CuO nanoparticles as deposited on the glass. In FIG. 2B, 16 represents the surface of the glass after heating, sintering, to 600° C. as described herein. In FIG. 2C, 18 represents the Cu-nanoparticles after the 300° C., $H_2$ reduction.

Test Results

I. Antibacterial

Definition: Log reduction=$-Log(C_a/C_0)$, where $C_a$ is the concentration of bacteria (or virus or fungus) after exposure to the antimicrobial surface and $C_0$ is the concentration of bacteria of the control sample which is not in contact with an antimicrobial surface.
Example: Log Reduction of 5=99.999% of bacteria killed.

The bacterial tests were carried out using $E$ $coli$ at a rate of $1\times10^6$ cells/ml. The cells were placed on the selected surface for 6 hours before being counted to determine how many remained alive. The conditions were the standard $E.$ $coli$ culture conditions of The following Table 1 shows anti bacterial behavior with $E.$ $coli$ within 6 hr with $1\times10^6$ cells/ml. Samples 29-39 CuO nanoparticles made according to Method 1 and are shown in Table 1. No easy-to-clean coating was applied.

TABLE 1

| | CuO wt % | Speed | Log Reduction |
|---|---|---|---|
| 29 | 5 | 50 | >5 |
| 30 | 5 | 50 | >5 |
| 31 | 2, 5 | 50 | >5 |
| 32 | 2, 5 | 50 | >5 |
| 33/34 | 1 | 50 | >5 |
| 35 | 0.5 | 50 | >5 |
| 36 | 0.5 | 50 | >5 |
| 37 | 0.5 | 50 | >5 |
| 38 | 0.5 | 25 | >5 |
| 39 | 0.5 | 25 | >5 |

1. CuO wt % is weight percent copper in the dip-coating solution.
2. Speed = withdrawal speed of the glass in mm/minute from the dip-coating solution.

Table 2 shows the $E.$ $coli$ test results obtained with five samples that were made by Method 1. No easy-to-clean coating was applied.

TABLE 2

| Sample | CuO wt % | Speed | Log Reduction |
|---|---|---|---|
| 132 | 1 | 50 | >5 |
| 133 | 1 | 50 | >5 |

TABLE 2-continued

| Sample | CuO wt % | Speed | Log Reduction |
|---|---|---|---|
| 134 | 1 | 50 | >5 |
| 135 | 1 | 50 | >5 |
| 136 | 1 | 50 | >5 |

1. CuO wt % is weight percent copper in the dip-coating solution.
2. Speed = withdrawal speed of the glass in mm/minute from the dip-coating solution Table 3 shows the $E.$ $coli$ test results obtained with five samples that were made according to Method 2 with a fluorosilane as an easy-to-clean coating in some examples.

TABLE 3

| Sample* | CuO %† | 650° C. Treatment | $H_2$ | Auto | Easy-to-clean Coating | IX | Log Reduction |
|---|---|---|---|---|---|---|---|
| 121 | 1 | Air | Yes | No | Yes | No | >5 |
| 122 | 1 | Air | Yes | No | No | No | >5 |
| 174 | 5 | Air | Yes | No | Yes | No | >5 |
| 175 | 5 | Air | Yes | No | No | No | >5 |
| 162 | 5 | $N_2$ | Yes | Yes | No | No | >5 |
| 163 | 5 | $N_2$ | Yes | yes | Yes | No | >5 |

*= For all samples the withdrawal speed of the glass from the dip-coating solution was 50 mm/minute.
†= Cu and $Cu^{+1}$.

II. Antiviral Testing Protocol

Viruses and Cell Lines

Adenoviral particles (Ad-CMV-eGFP) were purchased from Vector Biolabs (Philadelphia, Pa.). Herpes simplex virus, Type 1 was purchased from American Type Cell Culture (ATCC). Influenza A virus (strain WSN) was kindly supplied by Tom Shenk, Princeton University. Viral assay was performed in HeLa cells for Adenovirus, VERO cells for HSV and MDCK cells for Influenza virus. HeLa, VERO and MDCK cell lines were obtained from ATCC. HeLa and VERO cells were grown in Earle minimum Essential medium (EMEM) supplemented with 10% fetal bovine serum (FBS), 4.5 g/liter glucose, 2 mM glutamine, and antibiotics.

Anti-Viral Testing

Glass slide samples are placed in a polystyrene Petri dish (35 mm). A 10 ul droplet of virus solution diluted in D-PBS at a final concentration of $10^8$ PFU/ml was deposited to the center of the slide. A non-coated glass slide was placed on top and pressed to spread the droplet between the slides. Viruses were incubated at room temperature for 30 minutes to 1 hour. Slide glass exposed to the virus will be then thoroughly washed with 1 ml of D-PBS. Viruses were then diluted (twofold serial dilutions) with PBS. Samples are kept on ice to maintain virus titer until viral inoculation.

Determination of Virucidal Activity

Viral titration was performed by Plaque Assay for Influenza type A virus and HSV and by fluorescence microscopy for Adenovirus.
HSV Titration: Viruses exposed to glass samples were washed with EMEM with 2% FBS and serial diluted in the same medium. The day before the assay, 24-well plates of freshly confluent Vero cells were prepared. Culture was removed from each well prior to inoculation with 0.2 ml of the diluted HSV suspension. Viruses were allowed to adsorb at 37° C. in incubator with 5% $CO_2$ for 75 min. Plates were gently rocked back and forth every 15 min. The virus suspension was then removed and replaced with 1 ml of 0.4% agarose, EMEM 2% FBS. Agarose overlay was allowed to gel at room temperature for 1 h before placing plates in the incubator. Plates were incubated for 72 hours at 37° C. in a humidified atmosphere of 5% $CO_2$. Viral infection was evaluated by plaques formation.

Influenza Titration: Viruses exposed to glass samples were washed with D-PBS containing 0.2% BSA, 1% penicillin/streptomycin and 0.01% $CaCl_2$ and $MgCl_2$ and serial diluted in the same medium. The day before the assay, 24-well plates of freshly confluent MDCK cells were prepared. Culture was removed from each well and washed with buffer described above, prior to inoculation with 0.05 ml of the diluted HSV suspension. Viruses were allowed to adsorb at 37° C. in incubator with 5% $CO_2$ for 60 min. Plates were gently rocked back and forth every 15 minutes. Virus suspension was then removed and replaced with 1 ml of 1% agarose, DMEM, 0.4% FBS and 20 mM Hepes. The agarose overlay was allowed to gel at room temperature before placing plates in the incubator. Plates were incubated for 72 hours at 37° C. in a humidified atmosphere of 5% $CO_2$. Viral infection was evaluated by plaques formation.

Adenovirus Titration: Viruses exposed to glass samples were washed with EMEM w/o serum and serial diluted in the same medium. The day before the assay, a 96-well plate of freshly confluent HeLa cells were prepared. Culture was removed from each well prior to inoculation with 0.05 ml of the diluted adenovirus suspension. Viruses were allowed to adsorb at 37° C. in incubator with 5% $CO_2$ for 20 hours. Viral suspension was then removed and replaced with 1 ml of EMEM, 10% FBS, 1% L-Glutamine and 1% Pen/Strep. Plates were incubated for 24 hours at 37° C. in a humidified atmosphere of 5% $CO_2$. Viral infection was evaluated by fluorescence microscopy.

Virucidal Activity Calculation:

Log Reduction=Log 10 (Titer Virus Control/Titer Virus Sample)

% Reduction=(1−(Virus sample/Virus Control))*100

TABLE 4

Adenovirus

| Samples* Number | Comments | Final Titer after Exposure (PFU/ml) | Virus Titer Reduction % | Log Reduction |
|---|---|---|---|---|
| 110 | Cu and $Cu_2O$† | 0 | 100 | 4.62 |
| 109 | Cu and $Cu_2O$†• | 0 | 100 | 4.62 |
| 114 | Cu† | 0 | 100 | 4.62 |
| 113 | Cu†• | 0 | 100 | 4.62 |
| 137 | Cu and $Cu_2O$‡ | 0 | 100 | 4.62 |
| Control | No Cu | 42090 ± 4889 | 0 | 0 |

*= Withdrawal speed from dip-coating bath was 50 mm/min for all samples.
†= CuO is 1 wt %
‡= CuO is 5 wt %
•= the surface is coated with an easy-to-clean material, for example a fluorosilane.

TABLE 5

HSV and Influenza Virus

| Samples* Number | Comments | Final Titer after Exposure (PFU/ml) | Virus Titer Reduction % | Log Reduction |
|---|---|---|---|---|
| 228 | Cu and $Cu_2O$† | 0 | 100 | 4.05 |
| 220 | Cu and $Cu_2O$† | 0 | 100 | 3.63 |
| 224 | CuO†• | 2100 ± 141 | 50 | 0.3 |
| Cont5ol | No Cu | | 0 | 0 |

*= Withdrawal speed from dip-coating bath was 50 mm/min for all samples.
†= Cu is 1 wt %
•= the surface is coated with an easy-to-clean material, for example a fluorosilane.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

In the following Methods A to C, unless specified otherwise, the glass on which the Cu-containing nanoparticles, and any additional materials such as the protective material, a polymer or a water dispersible material, were deposited was Corning 2318 chemically strengthened glass in which potassium ions had been ion-exchanged into the glass for sodium and lithium that may be present in the glass.

Method A

Figure 3A:
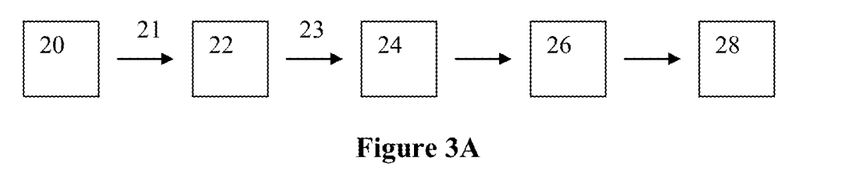
FIG. 3A is a flow sheet illustrating a first method, Method A, of preparing a glass article having metal or metal oxide nanoparticles thereon.

In Method A, as illustrated in FIG. 3A, water dispersed copper-containing nanoparticles were deposited onto a surface of an article by dipping, spraying or spin coating as represented by numeral 20 and the deposited particles were then dried on the glass article at a temperature in the range of 100° C. to 150° C. as represented by numeral 21. The drying time is in the range of 1 hour to 4 hours. The nanoparticle coated glass articles were then coated with protective coating material using spraying, dipping or spin coating as represented by numeral 22 and the articles having the protective coating thereon were then dried at a temperature in the range of 120° C. to 300° C. as represented by numeral 23. The drying time is in the range of 1 hour to 4 hours. Subsequently, as represented by numeral 24, the nanoparticles and protective coating were sintered onto the glass article in an atmosphere of air or an inert gas, for example nitrogen or argon, at a temperature in the range of 600° C. to 700° C. for a time in the range of 0.5 hours to 3 hours. In one embodiment the temperature was in the range of 600° C. to 650° C. Next the sintered glass of 24 was ion-exchanged, as represented by numeral 26, using an ion-exchange bath having alkali metal ions larger than the alkali metal ions present in the glass article. The ion-exchange was carried out at a temperature in the range of 370° C. to 450° C. for a time 10 minutes to 3 hours. After the ion-exchange, the glass article is cleaned and the metal nanoparticles on the glass are treated in a reducing atmosphere, for example hydrogen or forming gas, at a temperature in the range of 275° C. to 400° C. for a time in the range of 0.5 hour to 5 hours and a hydrogen or other reducing gas pressure in the range of 1-5 atmospheres. In one embodiment the reductions was carried out in a hydrogen at a temperature in the range of 275° C. to 325° C. for a time in the range of 1-2 hours and a hydrogen pressure of 1 atmosphere. In one embodiment the glass article onto which the nanoparticles were deposited as represent by numeral 20 was an ion-exchanged glass article having a compressive stress. Consequently, in the ion-exchange process as represented by numeral 26 the alkali metal in the ion-exchange of 26 can be the same size as the alkali metal use to impart the initial compressive stress. For example, if the glass article in 20 was a chemically strengthened glass prepared by ion-exchange of potassium ion for sodium and/or lithium ions in the glass, then potassium ions, or larger ions, can be used in the process step 26. The ion-exchange represented by 26 is carried out to impart a compressive stress to the protective coating layer, and also the glass.

As a specific example of Method A as depicted in FIG. 3A, a colloidal copper (II) oxide dispersion (NanoArc®, 23-37 nm average particle size powder, 97.5%, Alfa Aesar, Johnson Mathey Company, Wayne, Pa.) was obtained and dispersed in deionized (DI) water at concentrations of 0.5, 1, 1.5, 2.5 and 5 wt %. The colloidal suspensions were sonicated for a time in the range of 5 minutes to 30 minutes and then dip-coated onto samples of cleaned Corning 2318 glass (Corning Incorporated), which is a chemically strengthened aluminosilicate glass, to prepare nanoparticle-containing samples using foregoing nanoparticle suspension concentrations, numeral 20. The dip-coating was carried out at dip withdrawal speeds of 10, 25, 50 and 100 mm/min. In the dip-coating process the coating thickness generally increases with faster withdrawal speeds. The coated glass samples were then dried at 120° C. for 2 hours, numeral 21, and then coated with the protective coating material numeral 22. Two protective coatings materials were selected. The first materials were sodium silicates, also called herein NaSil, having a varying $SiO_2$ content and varying $SiO_2$/$Na_2O$ ratios (PQ Corporation, Malvern, Pa.) and the second materials were siloxanes, and in one embodiment methylsiloxanes (Honeywell Corporation, Morristown, N.J.). Both materials, as obtained, were diluted with their respective solvents to make solutions for dip-coating. The glass articles having nanoparticles thereon were dip-coated using the both NaSil and MS at varying speeds (25-100 mm/min). The samples were then dried at 300° C., numeral 23, and the nanoparticles and protective coating was sintered onto the 2318 glass in $N_2$ at 625° C., for a time in the range of 1-2 hours, numeral 24. After sintering the glass article having the nanoparticles and protective coating were ion-exchanged (IOX), numeral 26, using a $KNO_3$ bath at a temperature in the range of 370° C. to 450° C. for a time in the range of 10 minutes to 3 hours, provided that the starting glass articles was a chemically strengthened (ion-exchanged) glass. In an embodiment the ion-exchange was carried out at a temperature of 420° C. for a time of less than 1 hour. In another embodiment the ion-exchange time was less than 30 minutes. If the starting glass was not a chemically strengthened glass, then the ion-exchange was carried out at a temperature in the range of 370° C. to 450° C. for a time in the range of 5 hours to 8 hours; a typical ion-exchange time and temperature being 420° for 5.5 hours. Subsequently, the resulting glass article can then be used as-is or reduced in an atmosphere of hydrogen or other reducing gas, for example, forming gas at a temperature in the range of 275° C. to 350° C. for a time in the range of 1-2 hours as represented by numeral 28. In this example, after ion-exchange selected samples were reduced under $H_2$ at 300° C. for 1 hour.

Method B

Figure 3B:
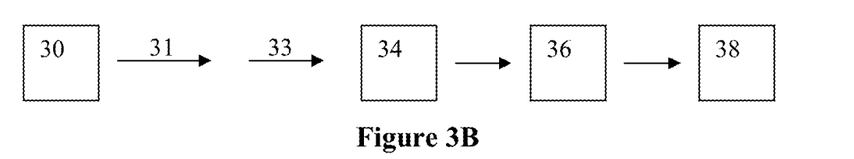
FIG. 3B is a flow sheet illustrating a second method, Method B, of preparing a glass article having metal or metal oxide nanoparticles thereon which combines two of the steps illustrated in FIG. 3A.

Method B is represented by FIG. 3B and in this method the steps represented by FIG. 3A numerals 20 in 22 were combined and the combination is represented in FIG. 3B by numeral 30. In FIG. 3B, numeral 30, the $Cu_2O$ or Cu nanoparticle dispersions and the protective material were mixed together, sonicated as described above and then coated or co-deposited (deposited simultaneously) onto a glass article by dip-coating, spraying, spin coating or slot coating. After the deposition was completed the glass coated with the nanoparticles and protective material was first dried at a drying temperature in the range of 100° C. to 150° C. for a time in the range of 1 hour to 4 hours as represented by numeral 31 and then coated glass was raised to the sintering temperature of 600° C. to 700° C. as represented by numeral 33 where the temperature was held for a time in the range of 0.5 hours to 3 hours represented by numeral 34 to sinter and adhere the coating, nanoparticles and protective material, to the glass article. In one embodiment the temperature was in the range of 600° C. to 650° C. After deposition of the copper and protective material, drying and sintering, the glass article was then ion-exchanged as represented by numeral 36 and a reduction of the nanoparticles was carried using hydrogen or other reducing gas at a temperature in the range of 275° C. to 350° C. for a time in the range of 1-2 hours represented by numeral 38. The glass articles may be used with or without the reduction step depending on the antimicrobial application. As an example, after ion-exchange the articles were reduced under 1 atmosphere of $H_2$ at 300° C. for 1 hour. The ion-exchange was carried out using a $KNO_3$ bath at a temperature in the range of 370° C. to 450° C. for a time in the range of 10 minutes to 3 hours. In an embodiment the ion-exchange was carried out at a temperature of 420° C. for a time of less than 1 hour. In another embodiment the ion-exchange time was less than 30 minutes. If the starting glass was not a chemically strengthened glass, then the ion-exchange was carried out at a temperature in the range of 370° C. to 450° C. for a time in the range of 5 hours to 8 hours; a typical ion-exchange time and temperature being 420° for 5.5 hours.

Method C

Figure 3C:
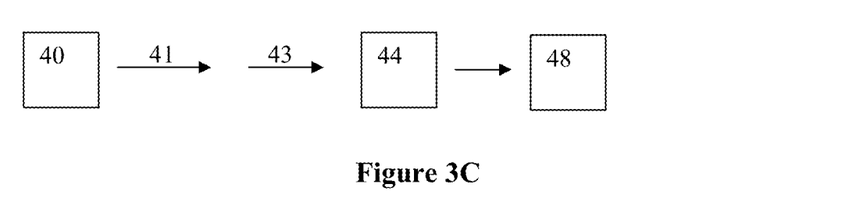
FIG. 3C is a flow sheet illustrating a third method, Method C, which can be used to prepare an article having metal nanoparticles, a protective material and a water dispersible material were mixed together and sonicated, and the mixture was then deposited on a glass article.

In Method C as illustrated in FIG. 3C, Cu nanoparticles, the protective agent and a water dispersible material were mixed together and sonicated, and the mixture was then deposited on a glass article by dip-coating, spraying, spin coating or slot coating as represented by numeral 40. The glass article with then deposited materials thereon was then dried as represented by numeral 41 at a drying temperature in the range of 100° C. to 150° C. and then heated, as represented by numeral 43, to a selected temperature in the range of 10-20° C. below the glass transition temperature $T_g$ of the water dispersible material in an atmosphere of $N_2$ or other inert gas, and held at the selected temperature below $T_g$ for a time in the range of 0.5 hours to 3 hours as represented by numeral 44. Subsequently, the resulting glass article can then be used as-is or reduced in an atmosphere of hydrogen or other reducing gas, for example, forming gas at a temperature in the range of 275° C. to 350° C. for a time in the range of 1-2 hours as represented by numeral 48. As an example, after ion-exchange the articles were reduced under 1 atmosphere of $H_2$ at 300° C. for 1 hour.

Protective Coating Protective Layer

The silicate protective materials used in reference to the following tables and figures were sodium silicate E (153-x and 56-x series, PQ Corporation) having a $SiO_2$ content of 27.2 wt %, the remainder being water, and a $SiO_2$/$Na_2O$ ratio of 3.2. Different NaSils are diluted to different concentrations while ensuring a consistent and stable pH range of 11-12. The 153-1 NaSil was the most concentrated and 56-6 was the most dilute used for the study. The effect of the concentration and the thickness are important parameters for this coating since the ultimate goal is to be anti microbial while preventing oxidation. The effect of the protectiveness was tested using environmental conditions such as 50° C./50% RH and keeping the sample immersed in water for 7 days.

In addition to sodium silicates, alkyl siloxanes can also be used as protective materials. As an example, methylsiloxane T111 (Accuglass resin, Honeywell Incorporated) was diluted with isopropanol and was also dip-coated onto the CuO nanoparticle coated surface, and was evaluated as a protective layer on Cu surface. The material was found to be satisfactory. As is the case for the NaSil coatings, the effect of the concentration and the thickness of the Methylsiloxane T11 are important parameters since the ultimate goal is to be anti microbial while preventing oxidation.

Figure 4:
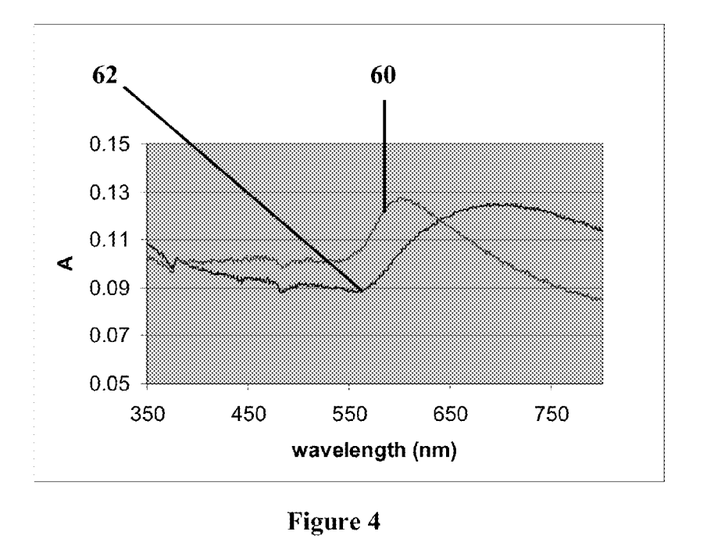
FIG. 4 is a graph of the absorption spectra for Cu nanoparticle surface before and after the treatment at 50° C./50% RH (relative humidity).

FIG. 4 is a graph of the absorption spectra for Cu nanoparticle surface before, line 60, and after the treatment at 50° C./50% RH (relative humidity), line 62, the graph showing that the Cu plasmon at 590 nm is red shifted with a broader, longer wavelength peak that appears after the 50/50 treatment, and further shows the appearance of slope at shorter wavelengths below approximately 450 nm that is believed to be the result of the oxidation of Cu to $Cu_2O$, Sample S316 has 2.5 wt % CuO nanoparticles deposited on the surface of the glass. The sample was sintered at 650° C., ion-exchanged and then reduced in $H_2$ at 300° C. for 1 hour.

Cu nanoparticle surfaces were kept in water for 7 day, with samples removed at days 1, 4 and 7, dried and their absorption measured. The Cu plasmon at 590 nm is shown to broaden, decrease and then disappear as the sample is kept in water for a longer time and converted to $Cu_2O$ or CuO, or both forms. The glass was prepared and after sintering at 650° C. in a $N_2$ atmosphere followed by ion-exchanged as described above and reduction in a $H_2$ atmosphere at 300° C. for 1 hour.

Figure 5:
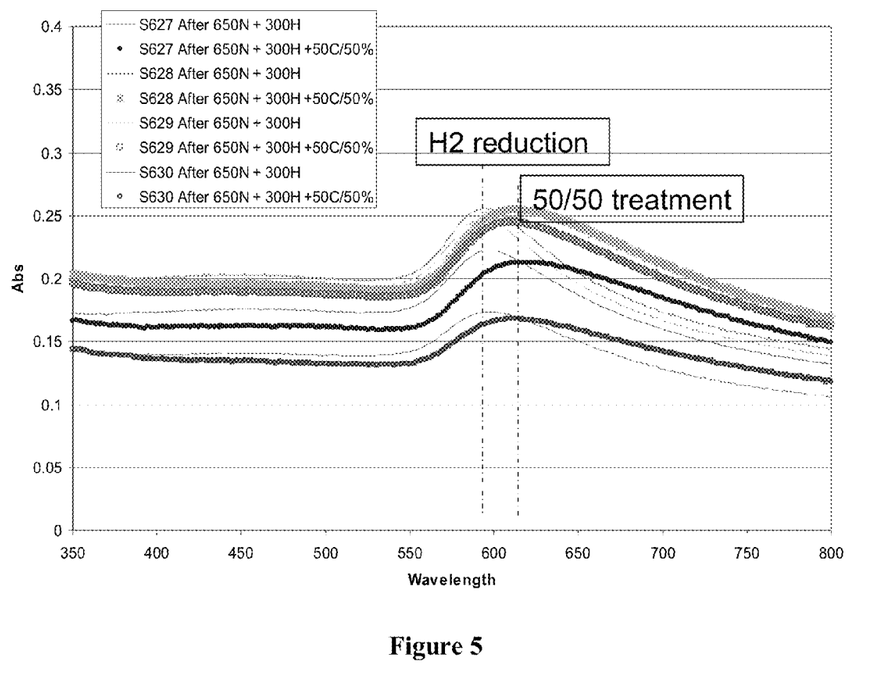
FIGS. 5 and 6 are graphs of the absorption spectra for the Cu nanoparticle-containing samples of Table 1 after hydrogen reduction only, FIG. 5, and after hydrogen reduction followed by treatment at 50° C. and 50% RH, FIG. 6.
Figure 6:
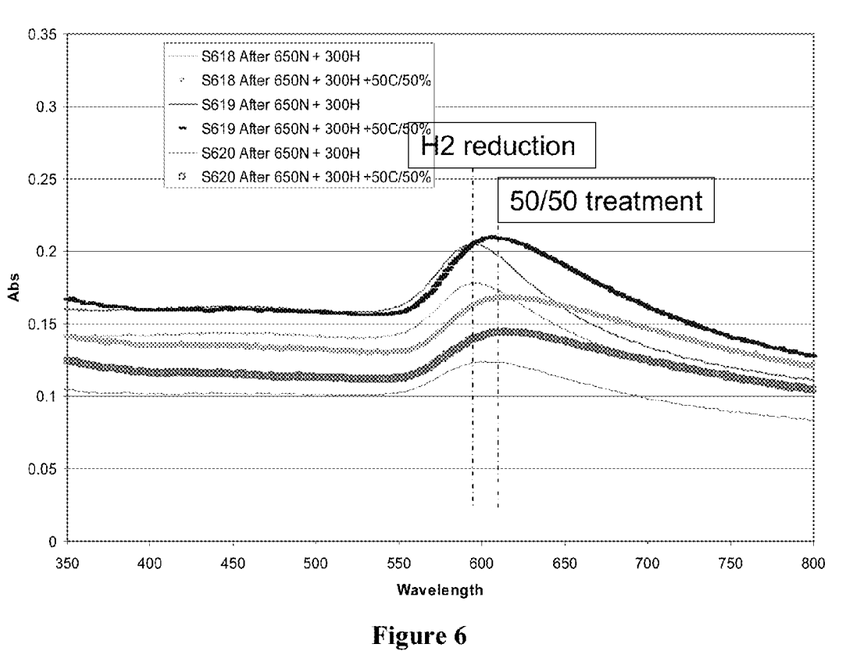

FIGS. 6 and 7 are graphs of the absorption spectra for the Cu nanoparticle-containing samples of Table 6 after hydrogen reduction only, FIG. 6, and after hydrogen reduction followed by treatment at 50° C. and 50% RH. In each Figure the broad lines represent the glass article after treatment at 50° C. and 50% RH and the narrow lined represent the glass article as prepared and before submersion in water. Sample reduction in hydrogen was carried out at 300° C. for 1 hour.

TABLE 6

| Sample # | CuO % | Coating | NaSil cure | | 650N | 30 0H | 50 C./50% RH |
|---|---|---|---|---|---|---|---|
| 618 | 1.5 | 56-4 | 1 hr@ 120 C./20 min | @300 C. | 650N | 30 0H | 50 C./50% RH 2 hr |
| 619 | 1.5 | 56-3 | 1 hr@ 120 C./20 min | @300 C. | 650N | 30 0H | 50 C./50% RH 2 hr |
| 620 | 1.5 | 56-1 | 1 hr@ 120 C./20 min | @300 C. | 650N | 30 0H | 50 C./50% RH 2 hr |
| 627 | 2.5 | 56-6 | 1 hr@ 120 C./20 min | @300 C. | 650N | 30 0H | 50 C./50% RH 2 hr |
| 628 | 2.5 | 56-4 | 1 hr@ 120 C./20 min | @300 C. | 650N | 30 0H | 50 C./50% RH 2 hr |
| 629 | 2.5 | 56-3 | 1 hr@ 120 C./20 min | @300 C. | 650N | 30 0H | 50 C./50% RH 2 hr |
| 630 | 2.5 | 56-1 | 1 hr@ 120 C./20 min | @300 C. | 650N | 30 0H | 50 C./50% RH 2 hr |

Figure 7A:
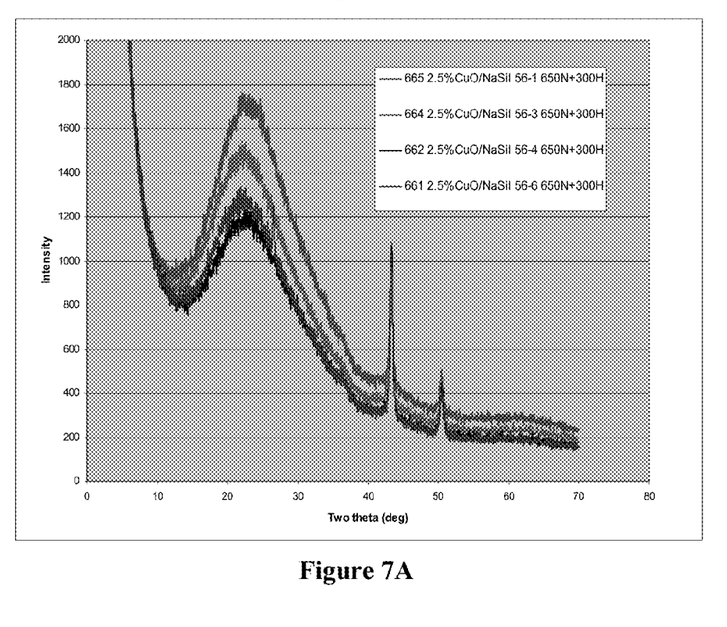
FIG. 7A is a graph of the GI-XRD (glancing incidence/x-ray diffraction) spectra, after hydrogen reduction, for a series of samples having 2.5 wt % Cu nanoparticles and a NaSil protective coating.
Figure 7B:
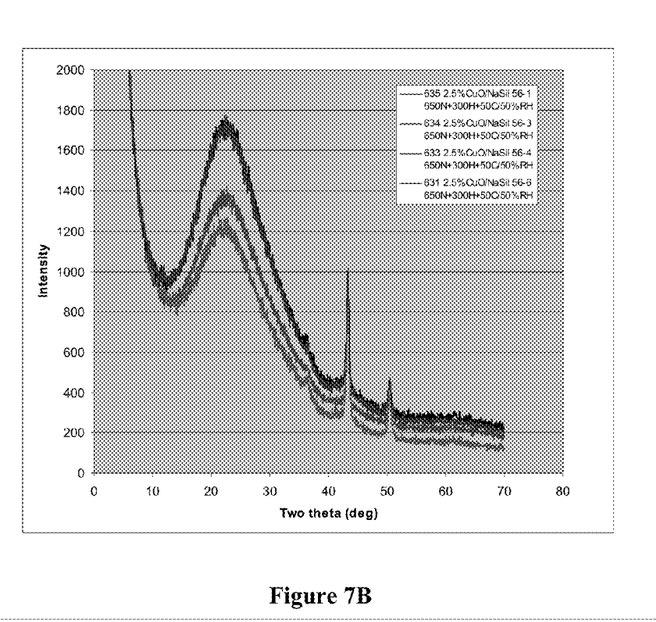
FIG. 7B is a graph of the GI-XRD spectra of the sample of FIG. 6 after they have undergone treatment at 50° C. and 50% RH.

FIG. 7A is a graph of the GI-XRD (glancing incidence/ x-ray diffraction) spectra, after hydrogen reduction, for a series of samples having 2.5 wt % Cu nanoparticles and a NaSil protective coating. FIG. 7B is a graph of the GI-XRD spectra of the sample of FIG. 6 after they have undergone treatment at 50° C. and 50% RH. Table 7 describes the samples used to obtain the data present in FIGS. 7A and 7B.

TABLE 7

| Sample | $H_2$ | 50° C./50% RH |
|---|---|---|
| 56-1 | Cu (43.2, 50.5) | Cu (43.4, 50.6) |
| 56-3 | Cu (43.3, 50.4) | Cu (43.4, 50.6) |
| | | $Cu_2O$ (36.45) |
| 56-4 | Cu (43.3, 50.5) | Cu (43.2, 50.5) |
| | | $Cu_2O$ (36.3 |
| 56-6 | Cu (43.2, 50.5) | Cu (43.3) and |
| | $Cu_2O$ (36.5) | quartz |

Samples contained 2.5 wt % CuO and NaSil
$H_2$ reduction was done at 300° C. for 1 hour.

As can be seen from FIGS. 7A and 7B and Table 7, the higher NaSil concentration Sample 56-1 shows no indication of an oxidized copper species at the surface of the glass after treatment at 50° C. and 50% RH.

Figure 8:
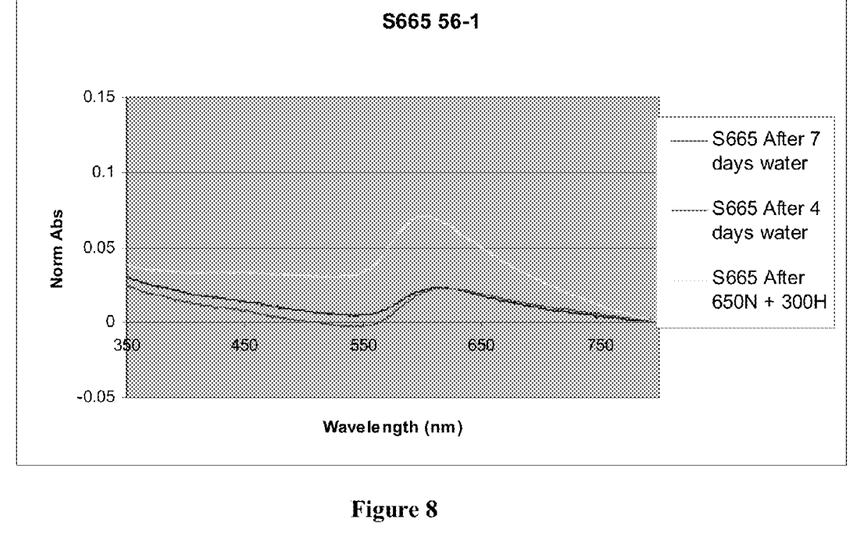
FIG. 8 is a graph of the absorption spectra of the Cu nanoparticle-containing surface having a NaSil protective coating thereon, sample 56-1, that was kept in water for 7 days. The sample was taken out of the water at day 4 and day 7, and its absorption was measured. The Cu plasmon at 590 nm is shown to decrease as the sample is kept in water for a longer time and the Cu was converted to $Cu_2O$ or $CuO$, or both forms.

FIG. 8 is a graph of the absorption spectra of the Cu nanoparticle-containing surface having a NaSil protective coating thereon, sample 56-1, that was kept in water for 7 days. The sample was taken out of the water at day 4 and day 7, and its absorption was measured. The Cu plasmon at 590 nm is shown to decrease as the sample is kept in water for a longer time and the Cu was converted to $Cu_2O$ or CuO, or both forms.

Antibacterial and Antimicrobial Testing

Table 8 shows antibacterial test results for Cu nanoparticle surfaces, after reduction, with a NaSil protective coating applied as described herein. Samples were prepared using two different CuO nanoparticles concentrations and varying concentrations of the protective coating are shown below. The test bacteria were *E. coli* at a concentration of $10^5$ bacteria/mL and the incubation time was 6 hours at a temperature of 37° C. The samples reduction was carried out in a temperature of 300° C. for 1 hour.

Table 9 shows antiviral test results using Adenovirus Type 5 (dE1/dE3), a non-replicating virus. The initial titer of virus exposed to a glass slide of the indicated Sample glass having Cu-containing nanoparticles or the Control was $10^6$ PFU/mL with an exposure time of 1-2 hours at a room temperature, RT, 18° C.-25° C. The glass samples before placement of the virus-containing titer were washed with ethanol but were not autoclaved.

Table 10 shows the different concentrations of NaSil that were used as the protective coating on the Cu surface.

TABLE 8

*E. coli.* Antibacterial Tests

| Sample Number | Dip-Coating Conditions | Post-Dip | Log Reduction |
|---|---|---|---|
| 685 | 2.5% Cu, 100 mm/min, 56-6 | IX/Reduced | 2.3 |

TABLE 8-continued

E. coli. Antibacterial Tests

| Sample Number | Dip-Coating Conditions | Post-Dip | Log Reduction |
|---|---|---|---|
| 689 | 2.5% Cu, 100 mm/min, 56-3 | IX/Reduced | 2.2 |
| 687 | 2.5% Cu, 100 mm/min, 56-4 | IX/Reduced | 2.1 |
| 691 | 2.5% Cu, 100 mm/min, 56-1 | IX/Reduced | 2.2 |
| 719 | 1% Cu, 50 mm/min, 56-6 | IX/Reduced | 2.2 |
| 721 | 1% Cu, 50 mm/min, 56-4 | IX/Reduced | 2.2 |
| 723 | 1% Cu, 50 mm/min, 56-3 | IX/Reduced | 2.3 |
| 725 | 1% Cu, 50 mm/min, 56-1 | IX/Reduced | 2.4 |
| 2318 control Soda lime | | | 0 |
| 5%, 20 min Ag/K | | | >5 |
| 901BFK 10% Cu | | | >6 |

TABLE 9

Adenovirus Type 5 (dE1/dE3) Test Results

| Samples | Final Titer after exposure (PFU/mL) | Virus Titer reduction % | Log Reduction |
|---|---|---|---|
| 618-1.5% CuO—650N/300H—NaSi coating 56-4 | 2185 ± 1150 | 99.07 | 2.03 |
| 618-1.5% CuO—650N/300H—NaSi coating 56-3 | 1610 ± 593 | 99.31 | 2.16 |
| 618-1.5% CuO—650N/300H—NaSi coating 56-1 | 3105 ± 948 | 98.67 | 1.87 |
| 618-1.5% CuO—650N/300H—NaSi coating 56-4 | 1840 ± 751 | 99.21 | 2.10 |
| 618-1.5% CuO—650N/300H—NaSi coating 56-3 | 1610 ± 880 | 99.31 | 2.16 |
| 618-1.5% CuO—650N/300H—NaSi coating 56-1 | 1495 ± 1472 | 99.36 | 2.19 |
| 375-1.5% CuO—650N + IOX+/300H | 1955 ± 1472 | 99.16 | 2.08 |
| 2318 Control | 235060 ± 20715 | 0 | 0 |

Samples 375 did not have a NaSil protective coating
The 2318 Control sample did not have any cu-containing nanoparticle deposited on its surface

TABLE 10

NaSil Protective Coating Concentration on Cu surface.

| NaSil Number | $Na_2O/SiO_2$, wt %/wt % |
|---|---|
| 153-1 | 3.3/10.6 |
| 153-2 | 6.6/21.2 |
| 56-1 | 1.65/5.3 |
| 56-2 | 0.82/2.65 |
| 56-3 | 0.4/1.3 |
| 56-4 | 0.2/0.65 |
| 56-6 | 0.07/0.21 |

Low Surface Energy Coatings

As a final step, the Cu-contain glass articles, or Cu—Ag containing glass articles, can be coated with a final coating of a low surface energy coating, such coating also being know as easy-to-clean coatings. For example, in many touch screen applications (phones, computers, ATMs, etc) where the glass is used as a cover glass, a coating or film is placed on the glass surface so that fingerprints can be cleaned relatively easily. The coating(s) that facilitate cleaning are low surface energy coatings, for example, coatings in the class of "fluoroalkylsilanes" of general formula $A_x$-Si—$B_{4-x}$, where A is selected from the group consisting of perfluoroalkyl $R_F$—, perfluoroalkyl terminated perfluoropolyether, perfluoroalkyl-alkyl, copolymers of fluoroalkene silanes and alkene silanes, and mixtures of fluoroalkylsilanes and hydrophilic silanes, B is Cl, acetoxy [$CH_3$—C(O)—O—] or alkoxy [for example $CH_3O$— or $C_2H_5O$—], and x=1 or 2. Low surface energy coatings of the foregoing types are commercially available from different manufacturers, for example, Dow Corning, [DC2634—a perfluoropolyether silane in which the functional perfluoro moiety is Poly[oxy(1,1,2,2,3,3-hexafluoro-1,3-propanediyl)], α-(heptafluoropropyl)-ω-[1,1,2,2-tetrafluoro-3-(2-propenyloxy)propoxy]; Gelest [SIT8174.0, Tridecafluorotetrahydrooctyltrichlorosilane; SIT8371.0, Trifluoropropyltrichlorosilane; SIH5841.0 Heptadecafluorotetrahydrodecyl trichlorosilane; and SIH5841.0 (heptadecafluoro-1,1,2,2-tetrahydrodecyl)trichlorosilane; SIH5841.5 (heptadecafluoro-1,1,2,2-tetrahydrodecyl)trimethoxysilane; and SIH5841.2 (heptadecafluoro-1,1,2,2-tetrahydrodecyl)triethoxysilane]; Cytonix [FSM 1200 Perfluoropolyether mono-silane; FSD 2500 Medium molecular weight perfluoropolyether di-silane; FSD 4500 High molecular weight perfluoropolyether polysilanes]. The low surface energy coating should have a spacer or skeletal chain length in the range of 1 nm-20 nm, the skeletal chain being carbon atoms or a mixture of carbon and oxygen atoms in the case of the perfluoropolyethers. In one embodiment the chain length is in the range of 2 nm to 20 nm. In a further embodiment the chain length is in the range of 1-10 nm. Other examples are (a) Copolymers of fluoroalkene silanes and alkene silanes; and (b) mixtures of fluoroalkylsilanes and hydrophilic silanes. Silanes other than the foregoing can also be used provided that they do not prevent water vapor from reaching the surface of the glass so that copper ions can be transported from the glass surface to the microbe to thereby kill the microbe or inhibit its growth.

Generally, the fluoro-containing coatings describe above have 1 or 2 fluorocarbon-containing moieties attached to the silicon and each of the moieties, independently, have a chain length in the range of 1 nm to 20 nm, and the chain may include oxygen atoms or sulphur atoms along the chain. In one embodiment the chain length is in the range of 2 nm to 20 nm. In a further embodiment the chain length is in the range of 1-10 nm. What is important for the coating is that at least part the fluorocarbon moiety be sufficiently distant from the surface so that water molecules can come into contact with the surface, pick up copper ions on the surface, and transport the copper ions to a microbe where they can be absorbed in to microbe and thus kill it or decrease its reproductive rate. Consequently, it is preferred that one or two fluorocarbon moieties be attached to the silicon atom and that the silicon atom be bonded to the glass by two or three Si—O bonds. For example, if the alkyl group of (a) above, which functions as a spacer or skeletal chain between the copper-containing glass surface and the fluorocarbon moiety, is too short, then hydrophobic fluorocarbon moiety can block water molecules from reaching the glass surface and thus copper ions cannot be transported from the surface to and into the microbe. In another instance, without being held to any particular theory, it is believed that the oxygen atoms in a perfluoropolyether alkoxy silane that has been bonded to the surface of the antimicrobial glass can facilitate the migration of water molecules by oxygen atoms along the chain to the surface where the water molecules can coordinate to copper ions and facilitate the ions transport to the microbe. An exemplary perfluoropolyether alkoxy silane is Dow Corning® 2634 used as 0.02-1 wt % solutions in a fluorinated solvent. After the coating material was applied to the antimicrobial glass article such as described herein, the coating was cured to adhere the coating to the surface of the glass article and finally sonicated in a fluorinated solvent (for example, Novec™ HFE7200, 3M Company) bath for a 3 minutes remove any unreacted coating material. The curing was done thermally by either heating the coated in an oven, for example, at 50° C., 50% RH, for a cure time as suggested by the manufacturer or by infrared heating of the coated articles. The coated article also can be heated in an oven at 120° C. for a time in the range of 30 minutes to 2 hours to cure the coating material to the glass surface. Finally, the article is sonicated in HFE7200.

The method and process for the deposition of these coatings is capable of controlling the thickness and morphology of the coating on the surface of the glass. Process methods and steps can be introduced where the coating was deposited in such a fashion either to be discontinuous or quasi-discontinuous. Such process methods include, but are not limited to, vapor deposition or spray coating through a predetermined coverage mask, ink jet printing, micro contact printing using a master which would allow the fluorosilane to be coated in specific regions, humidity curing to allow phase separation of the fluorosilane. When the coating is sufficiently thin it can be continuous. Thin continuous coatings can be deposited, for example, by dip, spray and vapor deposition followed by curing to adhere the silanes, and followed by ultrasound cleaning to remove un-reacted but physically adsorbed silanes. The foregoing procedures allow the antimicrobial action to persist in open uncoated areas, or in areas where the coating is very thin or the surface is coating-free while at the same time maintaining intended functional performance of the coating. In the case where the coating is continuous, the coating is relatively thin, having a thickness, in one embodiment, in the range of 0.5 nm to 20 nm in order for the antimicrobial activity of the glass surface to remain effective. In another embodiment the thickness of the coating is in the range of 0.5 nm to 5 nm. In a further embodiment the thickness of the coating is in the range of 1 nm to 3 nm. In the thin coating case a mixed self-assembled monolayer can be prepared on the surface using two silanes, where one silane is a fluoroalkylsilane and the other silane is a hydrophilic silane (for example, a polyethylene glycol containing silane), wherein the hydrophilic or "water loving" silane domains assist in the antimicrobial action by capturing water molecules and presenting them to the surface where the water can pick up copper ions for transport to the microbe. In one embodiment fluoro-oligoethylene glycol silanes can also be used, where the oligoethylene glycol part of the silanes can assist in capturing free water at the interface.

Glass Compositions

The provided glass article on which the nanoparticles and protective coating can be deposited is selected from the group consisting of soda lime glass, alkali aluminosilicate glass and alkali aluminoborosilicate glass articles. In one embodiment the provided glass is selected from glasses having a composition, before chemical strengthening using a 100% $KNO_3$ bath at a temperature in the range of 370° C. to 450° C. for a time in the range of 4 hours to 8 hours, of:

(a) 60-70 mol % $SiO_2$; 6-14 mol % $Al_2O_3$; 0-15 mol % $B_2O_3$; 0-15 mol % $Li_2O$; 0-20 mol % $Na_2O$; 0-10 mol % $K_2O$; 0-8 mol % $MgO$; 0-10 mol % $CaO$; 0-5 mol % $ZrO_2$; 0-1 mol % $SnO_2$; 0-1 mol % $CeO_2$; less than 50 ppm $As_2O_3$; and less than 50 ppm $Sb_2O_3$; wherein 12 mol %≤$Li_2O+Na_2O+K_2O$≤20 mol % and 0 mol %≤$MgO+CaO$≤10 mol %;

(b) 64 mol %≤$SiO_2$≤68 mol %; 12 mol %≤$Na_2O$≤16 mol %; 8 mol %≤$Al_2O_3$≤12 mol %; 0 mol %≤$B_2O_3$≤3 mol %; 2 mol %≤$K_2O$≤5 mol %; 4 mol %≤$MgO$≤6 mol %; and 0 mol %≤$CaO$≤5 mol %, and wherein 66 mol %≤$SiO_2+B_2O_3+CaO$≤69 mol %; $Na_2O+K_2O+B_2O_3+MgO+CaO+SrO$>10 mol %; 5 mol %≤$MgO+CaO+SrO$≤8 mol %; ($Na_2O+B_2O_3$)–$Al_2O_3$≤2 mol %; 2 mol %≤$Na_2O$–$Al_2O_3$≤6 mol %; and 4 mol %≤($Na_2O+K_2O$)–$Al_2O_3$≤10 mol %;

(c) 61 mol %≤$SiO_2$≤75 mol %; 9 mol %≤$Na_2O$≤21 mol %; 7 mol %≤$Al_2O_3$≤15 mol %; 0 mol %≤$B_2O_3$≤12 mol %; 0 mol %≤$K_2O$≤4 mol %; 0 mol %≤$MgO$≤7 mol %; and 0 mol %≤$CaO$≤mol %;

(d) 50 mol %≤$SiO_2$≤70 mol %; 8 mol %≤$Na_2O$≤16 mol %; 9 mol %≤$Al_2O_3$≤17 mol %; 2 mol %≤$B_2O_3$≤12 mol %; 0 mol %≤$K_2O$≤4 mol %; 0 mol %≤$MgO$≤4 mol %; and 0 mol %≤$CaO$≤0.2 mol %. wherein the alkali metal oxides and the alkaline earth metal oxides are modifiers and the ratio [(mol % $Al_2O_3$+mol % $B_2O_3$)÷Σ mol % modifiers] is greater than 1, that is:

$$[(\text{mol \%} \ Al_2O_3+B_2O_3) \div \Sigma \ \text{mol \% modifiers}] > 1; \text{ and}$$

(e) $SiO_2$>50 mol %; 11 mol %≤$Na_2O$≤25 mol %; 7 mol %≤$Al_2O_3$≤26 mol %; o mol %≤$B_2O_3$≤9 mol %; 0 mol %≤$K_2O$≤2.5 mol %; 0 mol %≤$MgO$≤8.5 mol %; and 0 mol %≤$CaO$≤1.52 mol %; wherein the foregoing are substantially lithium free.

After the foregoing glasses have been chemically strengthened they have a compressive stress of greater than 250 MPa. In one embodiment the compressive stress is greater than 500 MPa. In another embodiment the compressive stress is greater than 750 MPa.

In one embodiment, the glass article has a transmission of 70% or above, for example, 80% or above, for example, 90% or above. In one embodiment, the glass article made according to Method 1 has a transmission of 70% or above, for example, 80% or above, for example, 90% or above. Tables 11 and 12 correspond to various concentrations of CuO nanoparticles coated onto glass using various dip withdrawal speeds. Transmission and haze is measured as coated, after sintering and after the reduction step. Transmission and haze measurements based on ASTM D-1003 and ASTM D-1044. Broadband white light source corresponds to CIE Illuminant A (incandescent lamp) measured using HazeGuard Plus™. Transmission is the total amount of light passing through sample and haze is the amount of light transmitted and scattered outside a 2.5° angular cone

TABLE 11

| Sample | withdrawal speed mm/min | As made Haze % | As made Trans % | Sintered Haze % | Sintered Trans % | Red Haze % | Red. Trans % |
|---|---|---|---|---|---|---|---|
| 0.5% CuO | 50 | 13.06 | 78.3 | 2.23 | 91.5 | 1.60 | 89.6 |
| 0.5% CuO | 75 | 10.5 | 81.7 | 1.38 | 93.2 | 1.10 | 92.6 |
| 0.5% CuO | 100 | 9.72 | 82.8 | 1.07 | 93.6 | 1.03 | 93.1 |
| 0.5% CuO | 150 | 9.70 | 83.0 | 0.95 | 93.6 | 0.91 | 93.2 |
| 1% CuO | 50 | 13.34 | 76.86 | 2.70 | 91.3 | 0.91 | 91.5 |
| 1% CuO | 75 | 13.02 | 77.26 | 2.01 | 91.6 | 1.71 | 89.7 |
| 1% CuO | 100 | 13.34 | 76.94 | 2.30 | 91.4 | 1.87 | 88.8 |
| 1% CuO | 150 | 13.88 | 75.72 | 2.51 | 90.8 | 1.95 | 87.3 |
| 1.5% CuO | 50 | 17.46 | 73.6 | 3.37 | 89.5 | 2.52 | 85.1 |
| 1.5% CuO | 75 | 18.3 | 72.44 | 3.55 | 89.1 | 2.71 | 84.6 |
| 1.5% CuO | 100 | 18.6 | 70.98 | 2.21 | 90.5 | 1.64 | 87.0 |
| 1.5% CuO | 150 | 14.6 | 73.4 | 1.86 | 90.7 | 1.34 | 87.4 |
| 2.5% CuO | 50 | 19.7 | 70.8 | 3.50 | 88.3 | 2.37 | 85.0 |
| 2.5% CuO | 75 | 18.3 | 73.7 | 2.68 | 89.6 | 1.97 | 86.2 |
| 2.5% CuO | 100 | 18.0 | 72.4 | 2.41 | 90.6 | 2.20 | 86.3 |
| 2.5% CuO | 150 | 17.4 | 67.3 | 4.08 | 85.9 | 3.06 | 79.0 |
| 5% CuO | 50 | 18.5 | 68.3 | 3.77 | 87.5 | 3.00 | 80.4 |
| 5% CuO | 75 | 13.4 | 58.7 | 6.65 | 75.8 | 4.34 | 58.0 |
| 5% CuO | 100 | 14.8 | 55.9 | 7.95 | 72.8 | 5.71 | 52.4 |
| 5% CuO | 150 | 11.2 | 51.3 | 7.44 | 58.9 | 5.40 | 37.0 |

Sinter condition - 650 C., 1 h in N2
Reduction condition - 300 C., 1 h in H2

TABLE 12

| Sample | withdrawal speed | As made Haze % | As made Trans % | Sintered Haze % | Sintered Trans % | Red Haze % | Red. Trans % |
|---|---|---|---|---|---|---|---|
| 0.5% CuO w/ 0.001% Tergitol | 50 | 8.4 | 84.3 | 0.49 | 94.0 | 0.48 | 93.9 |
| 0.5% CuO w/ 0.001% Tergitol | 75 | 6.9 | 86.3 | 0.31 | 94.2 | 0.35 | 94.2 |
| 0.5% CuO w/ 0.001% Tergitol | 100 | 7.0 | 86.5 | 0.36 | 94.3 | 0.38 | 94.3 |
| 0.5% CuO w/ 0.001% Tergitol | 150 | 9.6 | 81.9 | 0.50 | 94.0 | 0.48 | 93.8 |
| 1% CuO w/ 0.001% Tergitol | 50 | 12.1 | 80.2 | 1.47 | 92.6 | 1.04 | 90.6 |
| 1% CuO w/ 0.001% Tergitol | 75 | 11.8 | 81.1 | 1.15 | 93.1 | 0.88 | 91.5 |
| 1% CuO w/ 0.001% Tergitol | 100 | 12.5 | 80.6 | 0.99 | 93.3 | 0.83 | 91.8 |
| 1% CuO w/ 0.001% Tergitol | 150 | 13.6 | 79.8 | 1.03 | 93.2 | 0.84 | 89.8 |
| 1.5% CuO w/ 0.001% Tergitol | 50 | 16.2 | 77.5 | 2.33 | 91.4 | 1.82 | 87.8 |
| 1.5% CuO w/ 0.001% Tergitol | 75 | 12.0 | 81.5 | 0.89 | 93.6 | 0.72 | 92.6 |
| 1.5% CuO w/ 0.001% Tergitol | 100 | 13.5 | 79.6 | 0.83 | 93.3 | 0.68 | 91.9 |
| 1.5% CuO w/ 0.001% Tergitol | 150 | 15.6 | 77.3 | 1.06 | 92.7 | 0.92 | 90.1 |
| 2.5% CuO w/ 0.001% Tergitol | 50 | 24.1 | 68.9 | 5.8 | 85.2 | 5.04 | 76.9 |
| 2.5% CuO w/ 0.001% Tergitol | 100 | 22.5 | 63.2 | 7.27 | 80.2 | 5.77 | 69.1 |

For use in consumer electronics such as cellphones, notebook and tablet computers and similar small devices, including touch sheen devices, the thickness of the final Cu-containing glass product is generally in the range of 0.2 mm to 52 mm. For other uses, for example, for use as antibacterial or antimicrobial shelving, table tops and other applications in hospitals, laboratories and other institutions handling biological substances, the thickness can be in the range of 0.5 mm to 2 cm depending on the exact application.

While typical embodiments have been set forth for the purpose of illustration, the foregoing description should not be deemed to be a limitation on the scope of the disclosure or the appended claims. Accordingly, various modifications, adaptations, and alternatives may occur to one skilled in the art without departing from the spirit and scope of this disclosure or the appended claims.

We claim:

1. An antimicrobial glass article comprising a glass substrate and copper-containing nanoparticles sintered on a surface of the glass, the copper-containing nanoparticles being selected from the group consisting of $Cu^0$ nanoparticles, $Cu_2O$ nanoparticles, and combinations thereof, wherein the glass has an antibacterial log reduction value ≥1 and an antiviral log reduction value ≥1.

2. The antimicrobial glass article according to claim 1, wherein the glass substrate is selected from the group consisting of alkali aluminosilicate glass, alkali aluminoborosilicate glass, soda lime glass, and combinations thereof.

3. The antimicrobial glass article according to claim 1, wherein the glass has an antibacterial log reduction value ≥3.

4. The antimicrobial glass article according to claim 1, wherein the glass is strengthened.

5. The antimicrobial glass article according to claim 1, further comprising a coating disposed on the surface of the glass.

6. The antimicrobial glass article according to claim 5, wherein the coating is selected from the group consisting of a fluorosilane coating, a sodium silicate coating and a siloxane coating.

7. The antimicrobial glass article according to claim 1, further comprising a coating disposed on the surface of the glass and on the copper-containing particles.

8. The antimicrobial glass article according to claim 7, wherein the coating is selected from the group consisting of a fluorosilane coating, a sodium silicate coating and a siloxane coating.

9. An antimicrobial glass article comprising a glass substrate and metal nanoparticles disposed on a surface of the glass, the metal nanoparticles being selected from the group consisting of copper(0), silver(0), nickel(0), platinum(0), palladium (0), gold(0) and zinc(0) particles, and a protective coating disposed on the metal nanoparticles, the protective coating selected from the group consisting of sodium silicates (NaSil) and poly siloxanes/silsesquioxanes,
 wherein the glass has an antibacterial log reduction value ≥1 and an antiviral log reduction value ≥1.

10. The antimicrobial glass article according to claim 9, wherein the glass substrate is selected from the group consisting of alkali aluminosilicate glass, alkali aluminoborosilicate glass, soda lime glass, and combinations thereof.

11. The antimicrobial glass article according to claim 10, wherein the glass is strengthened.

12. The antimicrobial glass article according to claim 9, wherein the glass has an antibacterial log reduction value ≥3.

* * * * *

UNITED STATES PATENT AND TRADEMARK OFFICE
CERTIFICATE OF CORRECTION

PATENT NO. : 9,439,439 B2
APPLICATION NO. : 14/682452
DATED : September 13, 2016
INVENTOR(S) : Nicholas Francis Borrelli et al.

Page 1 of 1

It is certified that error appears in the above-identified patent and that said Letters Patent is hereby corrected as shown below:

On the Title Page

In item (57), in Column 2, in "Abstract", Line 3, delete "include s" and insert -- includes --.

On the page 2, in Column 2, under "Other Publications", Line 11, delete "Nanatechnology" and insert -- Nanotechnology --.

On the page 2, in Column 2, under "Other Publications", Line 24, delete "cooper" and insert -- copper --.

On the page 2, in Column 2, under "Other Publications", Lines 36-37, delete "610 n." and insert -- 610. --.

In the Claims

In Column 23, Line 9, in Claim 9, delete "palladium (0)," and insert -- palladium(0), --.

Signed and Sealed this
Twenty-seventh Day of September, 2022

Katherine Kelly Vidal
*Director of the United States Patent and Trademark Office*